(12) United States Patent
Javid et al.

(10) Patent No.: US 11,090,315 B1
(45) Date of Patent: Aug. 17, 2021

(54) PREVENTION AND TREATMENT OF FLU-TYPE VIRAL INFECTIONS AND RELATED COMPLICATIONS

(71) Applicants: Mihan Jafari Javid, Tehran (IR); Amir Dadgari, Tehran (IR)

(72) Inventors: Mihan Jafari Javid, Tehran (IR); Amir Dadgari, Tehran (IR)

(*) Notice: Subject to any disclaimer, the term of this patent is extended or adjusted under 35 U.S.C. 154(b) by 0 days.

(21) Appl. No.: 16/994,632

(22) Filed: Aug. 16, 2020

Related U.S. Application Data

(60) Provisional application No. 62/991,324, filed on Mar. 18, 2020, provisional application No. 62/944,014, filed on Mar. 24, 2020.

(51) Int. Cl.

| | | |
|---|---|---|
| *A61K 31/585* | (2006.01) | |
| *A61K 31/192* | (2006.01) | |
| *A61K 31/375* | (2006.01) | |
| *A61K 9/00* | (2006.01) | |
| *A61K 36/28* | (2006.01) | |
| *A61K 31/167* | (2006.01) | |
| *A61K 31/4402* | (2006.01) | |
| *A61K 39/395* | (2006.01) | |
| *A61K 31/197* | (2006.01) | |
| *A61K 45/06* | (2006.01) | |
| *A61K 35/18* | (2015.01) | |
| *A61K 31/138* | (2006.01) | |

(52) U.S. Cl.
CPC .......... *A61K 31/585* (2013.01); *A61K 9/0019* (2013.01); *A61K 9/0073* (2013.01); *A61K 9/0095* (2013.01); *A61K 31/138* (2013.01); *A61K 31/167* (2013.01); *A61K 31/192* (2013.01); *A61K 31/197* (2013.01); *A61K 31/375* (2013.01); *A61K 31/4402* (2013.01); *A61K 35/18* (2013.01); *A61K 36/28* (2013.01); *A61K 39/395* (2013.01); *A61K 45/06* (2013.01)

(58) Field of Classification Search
CPC .. A61K 31/585; A61K 31/197; A61K 9/0095; A61K 31/167; A61K 9/0073; A61K 31/375; A61K 9/0019; A61K 36/28; A61K 31/192; A61K 31/4402; A61K 31/138; A61K 39/395; A61K 35/18; A61K 45/06

See application file for complete search history.

(56) References Cited

PUBLICATIONS

Verma et al. Proceedings of the National Academy of Sciences 2016, 113(13), 3609-3614 (Year: 2016).*
Wiersinga et al. JAMA review, 2020. 324(8):789-793 (Year: 2020).*
Smart et al. Inflammopharmacology, 2020 (28):1141-1152 (Year: 2020).*
Cadegiani et al. Medical Hypotheses 143, (Jul. 2020) 110112; pp. 1-7 (Year: 2020).*

\* cited by examiner

*Primary Examiner* — Dennis Heyer
(74) *Attorney, Agent, or Firm* — Barry Choobin; Patent 360

(57) ABSTRACT

The present invention is directed to composition and method for the treatment, prevention, or reducing the complication of flu-like viral infections, including SARS-Coronaviruses. The composition comprises ibuprofen, spironolactone, acetaminophen, chlorpheniramine, and phenylephrine.

10 Claims, No Drawings

PREVENTION AND TREATMENT OF FLU-TYPE VIRAL INFECTIONS AND RELATED COMPLICATIONS

CROSS-REFERENCE TO RELATED APPLICATIONS

This application claims priority to the U.S. provisional patent application Ser. No. 62/991,324, entitled "Compound Anti-flu Medicine: Prevention and treatment of flu type viral infections and complications" filed on Mar. 18, 2020 and U.S. provisional patent application Ser. No. 62/994,014, entitled "Chemo-herbal Preventive and Therapeutic Protocol for COVID 19 Infection and Related Complications" filed on Mar. 24, 2020, each of which is incorporated herein by reference in its entirety.

FIELD OF INVENTION

The present invention relates to a method of treatment, and in more particular, relates to a composition and a method for the treatment of infections due to SARS coronaviruses.

BACKGROUND

SARS (severe acute respiratory syndrome) coronavirus, abbreviated as (SARS-CoV) are viruses identified in 2003. The first human infected with SARS-CoV was in the Guangdong province of southern China in 2002. SARS-CoV is an animal virus, perhaps bats are the reservoir of the virus, which spread to other animals including humans. The transmission of SARS-CoV is primarily from human to human. These viruses generally target the respiratory system of a patient and show influenza-like symptoms. The symptoms include fever, malaise, myalgia, headache, diarrhea, and shivering (rigors). Fever is the most frequently reported symptom, however, none of the symptoms is specific for the SARS-CoV.

COVID-19 is a newly discovered coronavirus, appeared in Wuhan, a city in China, in December 2019. Symptoms of COVID-19 can range from mild-illness to pneumonia, renal dysfunction, multi-organ failure. Unlike the previous SARS-CoV, COVID-19 has proved to be more lethal. Currently, there is no specific antiviral treatment recommended for COVID-19. Patients infected with COVID-19 rely on their natural immunity and generally seek supportive care to help relieve symptoms. In severe cases, treatment involves mechanical ventilation and vital organ function support.

Thus, a need is appreciated for a composition for the prevention and treatment of SARS-CoV infections and their associated complications.

SUMMARY OF THE INVENTION

The principal objective of the present invention is therefore directed to a method for treatment of viral infection in a patient.

It is an objective of the present invention to provide a composition for the treatment of SARS-CoV infections.

It is an additional objective of the present invention that the composition can treat COVID-19 infection.

It is still an additional objective of the present invention that the method and composition provide symptomatic relief.

It is a further objective of the present invention that the method and composition prevent or minimize the complications associated with the COVID-19 infection.

It is yet another objective of the present invention that the composition can help to prevent and treat other flu-like infections.

In one aspect, the present invention is directed to a composition and method for the treatment of the flu-type viral infection. In particular, the present invention is directed to a composition and method for the treatment of the COVID-19 infection. The composition according to certain embodiments of the present invention comprises ibuprofen and spironolactone in effective amounts. The effective amount of ibuprofen can be in a range of about 200-400 mg and the effective amount of spironolactone can be in a range of about 25-50 mg.

In one aspect, the composition according to certain embodiments comprises ibuprofen, spironolactone, acetaminophen, and chlorpheniramine.

In one aspect, the composition according to certain embodiments comprises ibuprofen 200-400 mg, spironolactone 25-50 mg, acetaminophen 325 mg, and chlorpheniramine 2 mg.

In one aspect, the composition according to certain embodiments comprises ibuprofen 200-400 mg, spironolactone 25-50 mg, acetaminophen 325 mg, chlorpheniramine 2 mg, and phenylephrine 30 mg.

In one aspect, a method is provided for the treatment of flu-like viral infections, the method comprises administering to a patient a composition comprising ibuprofen and spironolactone.

In one aspect, the composition can be administered orally, wherein the orally administered composition can be formulated as tablets or capsules.

In one aspect, the composition can be administered orally by gavage through a nasogastric tube.

In one aspect, the composition can be administered by parenteral route to the patient showing severe symptoms or complications.

In one aspect, the method is for preventing viral infection and includes administering to the patient chamomile herb and Vitamin C. The chamomile herb can be taken by the patient as a tea or tincture.

In one aspect, the present invention is a method for treating mild viral infection. The method comprises orally administering to a patient a predetermined effective amount of ibuprofen, spironolactone, acetaminophen, chlorpheniramine, and optionally phenylephrine. The method further comprises administering to the patient chamomile herb and Vitamin C. The chamomile herb can be taken by the patient as a tea or tincture.

In one aspect, the present invention is a method for treating moderate to severe viral infection. The method comprises administering, by oral or parenteral route, to a patient a predetermined effective amount of ibuprofen, spironolactone, acetaminophen, chlorpheniramine, and optionally phenylephrine. The method further comprises administering to the patient chamomile herb and Vitamin C. The chamomile herb can be taken orally or through inhalation of the chamomile tincture. The method further comprises administering by a parenteral route to the patient the effective amounts of amino acids, lipid emulsions, intravenous immunoglobulin, and packed red blood cells.

These and other objects and advantages of the embodiments herein will become readily apparent from the following detailed description.

DETAILED DESCRIPTION

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as compositions or methods of treatment. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Unless otherwise indicated, all numbers expressing quantities of ingredients used in this disclosure are to be understood as being modified in all instances by the term "about." Accordingly, unless indicated to the contrary, the numerical parameters set forth in this disclosure are approximations that may vary depending upon the desired properties sought to be obtained by the present disclosure. At the very least, and not as an attempt to limit the application of the doctrine of equivalents to the scope of any claims, each numerical parameter should be construed in light of the number of significant digits and ordinary rounding approaches.

Definitions

"Effective amount": In general, the "effective amount" of an active agent or a pharmaceutical composition refers to the amount necessary to elicit the desired biological response. As will be appreciated by those of ordinary skill in this art, the effective amount of an agent may vary depending on such factors as the desired biological endpoint, the agent being delivered, the disease being treated, the subject being treated, etc. The "effective amount" may also vary from person to person and can be based on age and weight of the person. The "effective amount" may also be based on the delivery route for the active agent, such as oral and parenteral.

"Pharmaceutical composition" or "compositions": hereinafter refers to preparations which are in such a form as to permit the biological activity of the active agents to be unequivocally effective, and which contain no additional components which are toxic as administered to the patients.

"Subject": means an individual and preferably a human who needs either prophylactic and/or therapeutic treatment. As used herein, a "subject" is the same as a "patient," and the terms can be used interchangeably.

'Treatment": refers to medical treatment and includes both therapeutic and prophylactic treatment depending on the context of use herein. "Treatment" includes reducing the virus load, preventing, or reducing complications, and symptomatic relief.

"Synergistic": refers to a combination of active ingredients in the composition which results in greater improvement in the outcome of the treatment provided by the combination than provided by the individual ingredients of the composition when used independently of each other.

"Flu-like viral infection": included infections caused by viruses which effects respiratory system of a person and shows flu like symptoms. The flu like symptoms can include fever, malaise, myalgia, headache, and nasal congestion. It includes viral infection from SARS-CoV, COvid-19, and Middle East respiratory syndrome coronavirus (MERS-CoV).

"Prevention" means minimizing the chance that a subject who has an increased susceptibility for developing viral infection will develop viral infection.

The present invention is directed to a method and composition for the treatment of flu-like viral infections. The flu-like viral infections include the infection caused by SARS-CoV. Furthermore, flu-like viral infections include the infection caused by COVID-19. Perhaps, the present invention preferably provides a method and composition for the treatment of COVID-19 infection in a patient. The composition according to the present invention comprises spironolactone and ibuprofen.

Spironolactone, also known as 7α-acetylthiospirolactone, is a steroidal 17α-spirolactone having a molecular formula "C24H32O4S" and the IUPAC name "S-[(7R,8R,9S,10R, 13S,14S,17R)-10,13-Dimethyl-3,5'-dioxospiro[2,6,7,8,9,11, 12,14,15,16-decahydro-1H-cyclopenta[a]phenanthrene-17, 2'-oxolane]-7-yl] ethanethioate". Ibuprofen is a propionic acid-based non-steroidal anti-inflammatory drug. Chemically, it is "2-(4-Isobutylphenyl)propanoic acid", having a molecular formula "15687-27-1". In one exemplary embodiment, one or more active ingredients can be formulated into a composition in a neutral or salt form.

The method of treatment includes treating, preventing, providing symptomatic relief, reducing the severity of, or reducing complications of a viral infection. Alternatively, the method of treatment can include two stages: treatment of COVID 19 infection and treatment of complications of the infection such as cardiopulmonary complications, CNS complications, and other systemic involvements. In one case, the treatment can be based on symptoms and the degree of illness. For example, methods can be provided for the treatment of mild illness and severe illness. The mild illness may include headache, weakness, low to moderate fever, and dry cough. Severe illness includes, in addition to the above symptoms, trouble breathing. In case of severe illness, hospitalization of the patient may be advised. Other symptoms of severe illness may include persistent pain or pressure in the chest, sudden confusion or inability to arouse, bluish lips or face. While patients with mild symptoms can be treated at home, in case of severe symptoms, hospitalization is generally advised.

In one embodiment, the present invention is a method for preventing viral infections in humans. Preferably, the method is to prevent viral infections due to SARS CoV, such as Covid-19 viral infections. The method comprises frequently disinfecting the hands and mouth of a person using a viral disinfectant, such as isopropyl alcohol. Intake of chamomile tea at least twice a day. Chamomile tea can be prepared by boiling about 5 g of chamomile herb in approximately 200 ml of water for 2-3 minutes. Alternatively, can be administered chamomile tincture diluted in water. The method further includes administering Vitamin C at least one time daily. Oral intake of 500-1000 mg of Vitamin C is preferred.

In one embodiment, the present invention provides a method for the treatment of mild-illness due to a viral infection. Perhaps the mild-illness due to SARS COV including Covid-19 infection. The method includes administering to the patient chamomile tincture or chamomile tea and Vitamin C as discussed above for the prevention of the viral infection. Chamomile tea also helps in reducing the viral load in the body and provides symptomatic relief. The method further comprises orally administering to the patient, the composition of the present invention i.e. spironolactone and ibuprofen. Early treatment may be advised, especially in patients with underlying chronic disorders such as lung or heart disease, renal failure or immune compromising conditions to prevent threatening and/or lethal complications.

The effective dose of spironolactone in the composition can be about 25-50 mg. The effective doses of ibuprofen in the composition can be about 200-400 mg. It is to be understood by a skilled person that the effective dose can be determined based on the age and weight of a patient. Perhaps, the exact dose can be titrated based on the patient's response to the treatment with the composition of the present invention. In one exemplary embodiment, the effective dose of ibuprofen for a child can be about 5 to 10 mg/kg orally administered every 6 to 8 hours as needed. Wherein, the maximum dose can be 40 mg/kg/day or 4 doses per day. For adults, the effective dose of ibuprofen can be about 200-400 mg every 4 to 6 hours, and the maximum dose can be 1200 mg/day. The pediatric effective dose of Spironolactone can be about 1-3.3 mg/kg/day orally not to exceed 3.3 mg/kg/day or 100 mg/day.

In one case wherein the patient is an adult, ibuprofen in tablet form can be administered to the patient in a dose of 400 mg thrice a day. This dosage can be increased 2-3 times if the symptoms become moderate or severe. The spironolactone can be administered orally to the patient having a mild illness in a dosage of 25 mg twice a day. This dosage can also be increased 2-3 times if the symptoms become moderate or severe. Instead of a tablet, a suspension, syrup, or capsule can also be formulated. Also, for patients with chronic renal dysfunction, wherein the patient is additionally on any other therapy, such as ACE inhibitors, the patient can be monitored for hyperkalemia and checked at least weekly. Although the above dosage has been described for an adult patient, in case of children the dosage can be adjusted based on age and weight, for example, spironolactone dosage in children can be about 1-3 mg/kg once or twice a day, based on the severity of illness.

In another embodiment, the composition according to the present invention can additionally comprise acetaminophen, chlorpheniramine, and optionally phenylephrine. Acetaminophen, also commonly known as Paracetamol is known for the treatment of pain and fever. Chemically, it is a part of the class of drugs known as "aniline analgesics"; having molecular formula "$C_8H_9NO_2$" and the IUPAC name "N-(4-hydroxyphenyl)acetamide". Chlorpheniramine is a known antihistaminic drug having molecular formula "$C_{16}H_{19}ClN_2$" and IUPAC name "3-(4-Chlorophenyl)-N,N-dimethyl-3-pyridin-2-yl-propan-1-amine". Phenylephrine is also a known nasal decongestant having molecular formula "$C_9H_{13}NO_2$" and IUPAC name "(R)-3-[-1-hydroxy-2-(methylamino)ethyl]phenol".

The effective amount of acetaminophen in an oral composition can be 325 mg. In one case, the pediatric dose of orally administered acetaminophen can be about 10 to 15 mg/kg orally every 4 to 6 hours as needed not to exceed 5 doses in 24 hours. The adult dose of orally administered acetaminophen can be about 325 mg to 1 g orally every 4 to 6 hours not exceeding 4 g per day. Pediatric dose for chlorpheniramine can be about 0.5 mg to 2 mg every 4 to 6 hours not exceeding 16 mg/day. The adult dose of chlorpheniramine can be about 4-8 mg orally every 4 to 6 hours, not exceeding 32 mg/day. It is appreciated by a skilled person is that the maximum dose of an active ingredient is the dose above which toxicity outweigh the benefits.

The method for treating the patient with a mild illness can further include administering to the patient chlorpheniramine and acetaminophen. Both can be administered orally in a tablet or syrup form. Syrup may be preferable for children. The dosage can be adjusted based on the severity of the illness. Furthermore, in case the patient is having anxiety, chlordiazepoxide in a dosage of 5-10 mg can be administered orally to the patient twice a day. The chlordiazepoxide can be substituted by any other tranquilizers. In case, the patient is having nausea and vomiting, antiemetics such as metoclopramide and ondansetron in approved doses can also be administered to the patient.

In one embodiment, the present invention provides for the treatment of patients having a severe illness. Perhaps the present invention also provides for the treatment of hospitalized patients. The method as described above for the treatment of mild illness can be applied in severe illness, wherein the effective amount of the drugs either in the composition or administered separately can be increased 2-3 times based on the condition of the patient. The dosage can also be titrated based on the outcome of the treatment. Furthermore, alternate to orally administered the drugs or the composition, preferably, the composition can be administered by gavage through a nasogastric tube. In case, the intravenous dosage of one or more of the drugs is possible, the same could also be administered intravenously. A skilled person will, however, understand that the dosage of parenteral administration can be different from the oral administration. Thus, spironolactone and ibuprofen can be administered to the patient through gavage. Additionally, acetaminophen and chlorpheniramine can also be administered. Optionally, phenylephrine can also be administered to the patient, provided the patient does not have any reported adverse effects to the phenylephrine. Additionally, chamomile and Vitamin C can also be administered as described above for preventive treatment. In case, the patient is not on a ventilator, inhalation of chamomile tincture 1% through a nebulizer for 10 minutes 2-3 times a day can be administered. Also, as discussed above for mild-illness, tranquilizers and antiemetics can be additionally administered to the patient based on the symptoms.

The method for the treatment of the patient with severe illness further includes administering parenteral amino acids to the patient. The dosage and composition of parenteral amino acids are known to a skilled person for acute respiratory distress syndrome or systemic inflammatory response syndrome. Furthermore, lipid emulsions can be parenterally administered to the patient. The dosage and composition of lipid emulsions are known to a skilled person for acute respiratory distress syndrome or systemic inflammatory response syndrome. Intravenous immunoglobulins (IVIG)

can also be administered to the patient based on the symptoms. The dosage and composition of IVIG are known to a skilled person for a standard immunoglobulin therapy in immunoglobulin deficient patients. Furthermore, if the patient has low hemoglobin, in one case less than 12 mg/dl, then packed red blood cells can also be administered to the patient to achieve this minimum requirement for maintaining enough oxygen delivery to vital organs and maintaining oxygen saturation. The treatment can be adjusted, for example, change in doses of the drugs, based on the symptoms. Furthermore, the treatment can be continued as described above for severe illness, for one week after the complete subsiding of symptoms.

In one embodiment, the compositions of the present invention can be formulated according to known methods for preparing pharmaceutically useful compositions. In general, the compositions of the present invention will be formulated such that an effective amount of the bioactive agent is combined with a suitable carrier in order to facilitate effective administration of the composition.

In accordance with the invention, pharmaceutical compositions comprise active agents, and one or more non-toxic, pharmaceutically acceptable carriers or diluents. Pharmaceutical carriers or excipients may contain inert ingredients that do not interact with the active ingredients, or ingredients that do interact with the active ingredients. In general, the formulations are prepared by uniformly and intimately bringing into association the active ingredient with a liquid or solid carrier.

In one exemplary embodiment, the composition according to the present invention can be formulated as an oral composition and/or parenteral composition. The oral compositions, including tablets, capsules, suspensions, and syrups. The parenteral composition, including intravenous injection, infusions, subcutaneous injection, and intramuscular injection.

In one embodiment, sterile injectable solutions can be prepared by incorporating the active ingredients in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

Formulations for oral use include tablets containing the composition of the invention in a mixture with non-toxic pharmaceutically acceptable excipients. These excipients may be, for example, inert diluents, or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including.

Drugs may be mixed together in the tablet or may be partitioned. For example, a first drug is contained on the inside of the tablet, and a second drug is on the outside, such that a substantial portion of the second drug is released prior to the release of the first drug. Controlled release compositions for oral use may, e.g., be constructed to release the active drug by controlling the dissolution and/or the diffusion of the active drug substance.

In one embodiment, the present invention is directed a method for treating flu-like viral infection. The term treating included reducing the virus load in a subject, reducing the complications of the infection, and symptomatic relief. Also, the method according to the present invention provides for prevention of the viral infection. The method comprises administering to a patient an effective amount of a composition according to the present invention. In one case, the composition comprises an effective amount of Spironolactone and ibuprofen. In one case, the composition the comprises ibuprofen 200-400 mg, spironolactone 25-50 mg, acetaminophen 325 mg, chlorpheniramine 2 mg, and phenylephrine 30 mg.

The present invention is effective and economical in the treatment of flu-like viral infections. The treatment reduces virus loads, provides symptomatic relief, and reduces the probability of complications. In one case, the combination of spironolactone and ibuprofen is synergistic. In one case, the spironolactone and ibuprofen can be administered separately. In one case, the active ingredients ibuprofen, spironolactone, acetaminophen, chlorpheniramine, and phenylephrine can be administered as a combination. In other case, the active ingredients ibuprofen, spironolactone, acetaminophen, chlorpheniramine, and phenylephrine can be administered separately. When administered separated, one or more of the active ingredients including ibuprofen, spironolactone, acetaminophen, chlorpheniramine, and phenylephrine can be administered in one session or multiple session.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method for treating, providing symptomatic relief, reducing the severity of, or reducing complications of a SARS COVID-19 infection in a patient in need thereof, comprising administering to the patient a composition comprising a therapeutically effective amount of ibuprofen, spironolactone, chlorpheniramine, and acetaminophen.

2. The method of claim 1, the method further comprises:
administering to the patient, orally, chamomile tincture diluted in water, and Vitamin C in a range of 500-1000 mg per day.

3. The method of claim 1, wherein the method comprises orally administering to the patient the therapeutically effective amount of spironolactone, ibuprofen, chlorpheniramine, and acetaminophen.

4. The method of claim 3, wherein the therapeutically effective amount comprise ibuprofen 200-400 mg, spironolactone 25-50 mg, acetaminophen 325 mg, and chlorpheniramine 2 mg.

5. The method of claim 3, wherein the method further comprises administering to the patient an effective amount of chamomile herb and vitamin C.

6. The method of claim 5, wherein the chamomile herb is in a form of a tincture.

7. The method of claim 5, wherein the method further comprises administering orally to the patient an effective amount of an antiemetic drug.

8. The method of claim 1, wherein the method comprises administering to the patient by gavage through a nasogastric tube, the therapeutically effective amount of spironolactone, ibuprofen, chlorpheniramine, and acetaminophen.

9. The method of claim 8, wherein the method further comprises administering to the patient an effective amount of chamomile herb and vitamin C, wherein the chamomile herb is in a form of a tincture and administered by inhalation.

10. The method of claim 9, wherein the method further comprises administering to the patient an effective amount of packed red blood cells.

\* \* \* \* \*